United States Patent [19]

Semm

[11] Patent Number: 5,350,387
[45] Date of Patent: Sep. 27, 1994

[54] INSTRUMENT FOR APPLYING AN ADHESION PROPHYLAXIS FOR ENDOSCOPIC SURGERY

[75] Inventor: Kurt Semm, Kiel, Fed. Rep. of Germany

[73] Assignee: WISAP Gesellschaft fur wissenschaftlichen Apparatebau mbH, Sauerlach, Fed. Rep. of Germany

[21] Appl. No.: 955,197

[22] Filed: Oct. 2, 1992

[30] Foreign Application Priority Data

Oct. 2, 1991 [DE] Fed. Rep. of Germany ....... 4132855

[51] Int. Cl.$^5$ .............................................. A61B 17/08
[52] U.S. Cl. ................................... 606/151; 604/11; 604/13
[58] Field of Search ............... 604/170, 164, 167, 15, 604/16, 11-14; 606/151, 190, 198, 187; 600/37

[56] References Cited

U.S. PATENT DOCUMENTS

| 4,769,038 | 9/1988 | Bendavid et al. |
| 5,007,895 | 4/1991 | Burnett ................................ 604/11 |
| 5,037,379 | 8/1991 | Clayman et al. |
| 5,263,927 | 11/1993 | Shlain ................................... 604/13 |

FOREIGN PATENT DOCUMENTS

WO92/06638  4/1992  PCT Int'l Appl. .

OTHER PUBLICATIONS

Webster's New World Dictionary, 3rd Edition, 1988, p. 505.

*Primary Examiner*—John D. Yasko
*Assistant Examiner*—V. Alexander
*Attorney, Agent, or Firm*—Keck, Mahin & Cate

[57] ABSTRACT

An instrument for the application of an adhesion prophylaxis, particularly a film for endoscopic surgery, includes a circular cylindrical application sleeve for insertion in a trocar cannula or for direct insertion in a pneumoperitoneum. The application sleeve can receive a rod-like film carrier onto which is wound the film-like adhesion prophylaxis. For this purpose an elongated, particularly axial reception area, such as a slot is provided in the front area of the sleeve in which the adhesion prophylaxis is received in interlocking or frictional manner.

14 Claims, 1 Drawing Sheet

INSTRUMENT FOR APPLYING AN ADHESION PROPHYLAXIS FOR ENDOSCOPIC SURGERY

FIELD OF THE INVENTION

The invention relates to an instrument for applying an adhesion prophylaxis for endoscopic surgery.

BACKGROUND OF THE INVENTION

In conventional surgery, particularly in the abdominal region, it is known to insert a film in the abdomen in order to prevent the formation of adhesions between the internal organs and the abdominal wall.

The use of such adhesion prophylaxes, particularly in the form of films, would also be desirable for endoscopic surgery. However, it has not been possible hitherto, because it is necessary for the films to be folded to a very small size for entry into the incision and also to be unfoldable in a simple way to full size, after insertion.

SUMMARY OF THE INVENTION

An object of the invention is to provide an instrument of the aforementioned type, which permits the application of an adhesion prophylaxis, including for endoscopic surgery.

According to the invention, the instrument has a rod-like film carrier with a reception area for the interlocking or frictional reception of a film or a film end. In the simplest case the reception area can be in the form of an axial, elongated slot in the guide rod. The length of this elongated slot is preferably approximately 20 cm. The film is inserted approximately centrally into the elongated slot and is then rolled onto the film carrier by the rotation of the latter. The film carrier with the rolled up film is then introduced into an application sleeve, which can in turn be introduced by means of a trocar sleeve or cannula, or directly into the abdominal wall. Preferably the slotted area of the film carrier has a diameter of approximately 5 mm, whilst the application sleeve has an external diameter of approximately 10 mm. The wound up film is then located in the gap between the film carrier and the application sleeve. An unslotted area with a length of approximately 30 cm. is connected to the 20 cm long slotted area of the film carrier. The slotted film carrier area can consequently be moved from the approximately 20 cm long application sleeve completely into the abdomen and the film is opened out there by unwinding. The opening out of the film can be assisted by grippers, which are introduced by further trocar cannulas into the pneumoperitoneum.

When the reception area of the film carrier is constructed as an elongated slot, the film or an inflatable film cushion is inserted approximately centrally into the elongated slot, so that the film projects by approximately the same distance from the slot on both sides.

The film carrier reception area can also be constructed as a clamping device for receiving one longitudinal end of the film. In the reception area at least two engagement surfaces should be constructed, which can be pressed against one another, so that the longitudinal end of the film is secured. Release of the film following unrolling in the abdomen can only be brought about by the disengagement of the engagement surfaces.

The corners of the rolled up film are preferably fixed in the corresponding areas of the abdomen, so that film displacement is prevented. When using a cushion-like, inflatable film for a desired greater spacing of the internal organs from the abdominal wall, fixing can take place in a simple manner, because the dimensional stability of the film cushion exists per se.

The film or the cushion can be endoscopically removed, for example, after two to three days. Film removal can take place by using the instrument according to the invention.

The instrument permits an endoscopic introduction of the film, while leading to significant simplifications compared with the surgery used up to now. According to the prior art, the film has been introduced under general anesthesia and with cutting by means of a type of zipper. Almost every day there is a replacement of the film and/or an evaluation of the healing process in the vicinity of the film.

The film carrier permits the reception of both single, sterile, thin films and also multilayer films, which can be inflated as air cushions.

The use of an application sleeve, referred to as an applicator, permits an easier rotation of the film carrier for winding the film on and off. In the case of direct insertion of the film carrier into a trocar cannula, this rotation could be prevented by the cannula valve. When using the applicator, the cannula valve is automatically held in the open position through the outer wall of the applicator, so that the film carrier can be rotated without impediment.

The invention is described in greater detail with respect to the drawings.

DETAILED DESCRIPTION OF THE INVENTION

Figure 1:
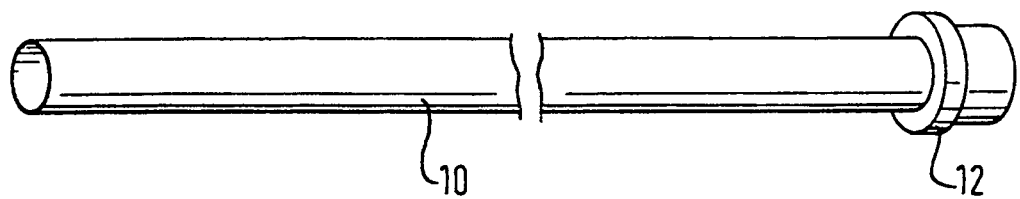
FIG. 1. is a perspective view of an application sleeve.
Figure 2:
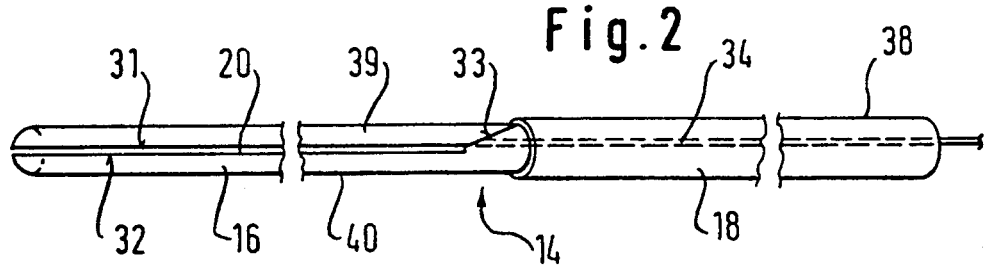
FIG. 2 is a perspective view of a rod-like film carrier for inserting in the applicator of FIG. 1.
Figure 3A:
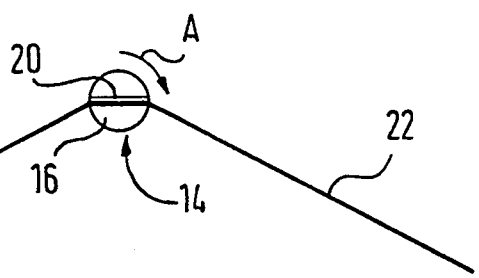
FIG. 3a is a front view of the film carrier at the start of the film winding process.
Figure 3B:
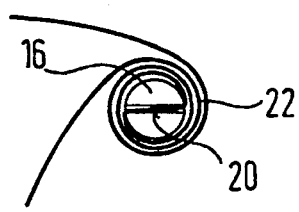
FIG. 3b is a front view of the film carrier during the film winding process.

FIG. 1 shows an application sleeve 10 with a stop ring 12 for engaging on the main body of a trocar cannula. The application sleeve 10 receives a film carrier 14 shown in FIG. 2. The film carrier 14 is subdivided into a longitudinally slotted front area 16 and a rear area 18. The slot has a length of approximately 20 cm and the rear, unslotted area 18 has a length of approximately 30 cm. The application sleeve 10 has a length of approximately 20 cm. The elongated slot 20 in the front area of the film carrier 14 serves as the reception area for a film 22 (FIG. 3). The slot has a width of, for example, about 0.5 to 2 mm, preferably about 1 to 1.5 mm.

Figure 3C:
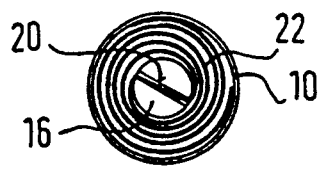
FIG. 3c is a front view of the film carrier at the end of the film winding process with the engaged application sleeve in place.

As shown in FIG. 3, the film is threaded into the elongated slot 20 of the film carrier 14 and then, by rotating the film carrier in the direction A, the film is rolled on the film carrier. As the film carrier 14 has an external diameter of approximately 5 mm and the thin-walled applicator 10 has an external diameter of approximately 10 mm, the rolled up film 22, as shown in FIG. 3c, is housed in the remaining free space. The applicator length is such that the entire length of the front, slotted area 16 of the film carrier 14 can be received in the applicator 10. With an external diameter of approximately 10 mm, the applicator 10 is appropriate for insertion in a trocar sleeve or cannula. The applicator 10 holds the film carrier in a rotatable manner, rotation not being impeded by the trocar cannula valve. Thus, the applicator 10 is engaged on the trocar cannula until the stop ring 12 strikes against the main body of the cannula. At its rear end the applicator can have a seal with respect to the film carrier 14, which prevents escape of gas between the applicator 10 and the rear end 18 of the film carrier 14. However, an escape of air can also be substantially prevented if the external diameter of the rear end 18 of the film carrier virtually corresponds to the internal diameter of the applicator 10.

Following forward axial movement of the film carrier 14 into the inside of the abdomen, the front area 16 of the film carrier 14 is moved out of the applicator 10. By subsequent rotation of the film carrier 14, the wound up film 22 is opened out in the abdomen and the opening out can be assisted by endoscopic instruments, such as grippers, which can be introduced through other trocar cannulas into the pneumoperitoneum.

The films can be made from biologically resistant material and/or from a material which dissolves over a period of time. The film prevents adhesions between the abdominal wall and the internal organs engaging on the abdominal wall in the period following an operation. The film can be removed after about 2 to 3 days by introducing the film carrier into the abdominal cavity and winding up the film. When using a self-dissolving film, no further endoscopic surgery is required. In principle, it is also conceivable to use the trocar cannula directly as the application sleeve, but this could impede film carrier rotation or make film carrier rotation more difficult.

According to an advantageous embodiment, the film carrier 14 comprises bearing surfaces 31, 32 between which the elongated slot 20 is located. The bearing surfaces 31, 32 are arranged in an adjustable manner against one another by an axial displacement of the upper front area 39 of the film carrier 14. The axial displacement is realized by a wedge-shaped surface 33 that allows an axial sliding movement of the upper front area 39 for reducing or broadening the width of slot 20. This axial displacement is controlled and fixed by a small rod 34 arranged within a bore of the unslotted area 18.

It is also shown that the proximal part of the film carrier 14 has a slightly larger diameter 38 than the diameter 40 of the front area 16.

Figure 4:
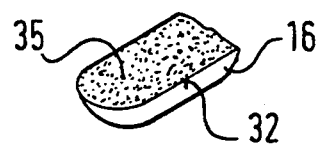
FIG. 4 is a perspective view of a broken away part of the lower front area of the film carrier.

The broken-away part in FIG. 4 shows a region of the lower front area 16 and a roughened surface 35 with which the bearing surface is provided. This roughened surface 35 allows a good contact between the film 22 and the bearing surface 32 and by this means improves the application of the adhesion prophylaxis.

Thus, as an endoscopic film applicator, an instrument according to the invention provides very advantageous adhesion prophylaxis for endoscopic surgery.

While the invention has been described with respect to certain embodiments thereof, it will be appreciated that variations and modifications may be made without departing from the spirit and scope of the invention.

What is claimed is:

1. An instrument for the application of an adhesion prophylaxis for endoscopic surgery, comprising a circular cylindrical application sleeve (10) for introduction into a trocar cannula or for direct introduction into a pneumoperitoneum, said sleeve (10) surrounding a rod-like film carrier (14) receiving a film-like adhesion prophylaxis (22), and an axially elongated reception area (20) at a forward end of the film carrier for receiving and winding up the adhesion prophylaxis (22).

2. An instrument according to claim 1, wherein said reception area (20) is adapted for interlocking and frictional reception of the adhesion prophylaxis (22).

3. An instrument according to claim 1, wherein the reception area (20) comprises an axially directed, elongated slot having a length of about 20 cm and a width of about 0.5 to 2 mm.

4. An instrument according to claim 3, wherein the width of the elongated slot is about 1 to 1.5 mm.

5. An instrument according to claim 3, wherein the application sleeve (10) and the elongated slot (20) are adapted for engaging together longitudinally.

6. An instrument according to claim 3, wherein the film carrier (14) comprises a rod having a total length greater than twice the length of the elongated slot (20).

7. An instrument according to claim 1, wherein a forward end of the film carrier (14) is rounded.

8. An instrument according to claim 1, wherein a seal is provided between the application sleeve (10) and the film carrier (14).

9. An instrument according to claim 1, wherein the film carrier (14) has a front and a rear area (16, 18), wherein the front area (16) is longitudinally slotted (20) and has a smaller external diameter than the rear area (18) and wherein the external diameter of the rear area (18) of the film carrier (14) substantially corresponds to the internal diameter of the application sleeve (10).

10. An instrument according to claim 1, further comprising a trocar cannula into which the instrument is introduced wherein the external diameter of the application sleeve (10) substantially corresponds to an internal diameter of the trocar cannula.

11. An instrument according to claim 10, wherein the application sleeve (10) has a radial, all-round stop region (12) for engagement on a main body of the trocar cannula.

12. An instrument according to claim 1, wherein the reception area comprises a slot.

13. An instrument according to claim 1, wherein bearing surfaces adjustable against one another are formed in the reception area.

14. An instrument according to claim 13, wherein the bearing surfaces comprise toughened surfaces for holding the adhesion prophylaxis.

* * * * *